United States Patent
Perra et al.

(10) Patent No.: US 8,300,372 B2
(45) Date of Patent: Oct. 30, 2012

(54) APPARATUS, SYSTEM, AND/OR METHOD FOR PROTECTION AND CONTROL OF AN ELECTRICAL DEVICE

(75) Inventors: Andre Pierre Perra, Portland, OR (US); Kent Jeffrey Holce, Portland, OR (US); Roger Steven Cota, Vancouver, WA (US)

(73) Assignee: Cerus Industrial Corporation, Hillsboro, OR (US)

( * ) Notice: Subject to any disclaimer, the term of this patent is extended or adjusted under 35 U.S.C. 154(b) by 494 days.

(21) Appl. No.: 11/784,117

(22) Filed: Apr. 4, 2007

(65) Prior Publication Data

US 2008/0094768 A1    Apr. 24, 2008

Related U.S. Application Data

(60) Provisional application No. 60/789,277, filed on Apr. 4, 2006.

(51) Int. Cl.
*H02H 3/00* (2006.01)
*H02H 9/02* (2006.01)

(52) U.S. Cl. .................... 361/79; 361/93.1; 361/93.2
(58) Field of Classification Search .............. 361/79, 361/93.1, 93.2
See application file for complete search history.

(56) References Cited

U.S. PATENT DOCUMENTS

| | | | | |
|---|---|---|---|---|
| 4,894,588 A * | 1/1990 | Stack | ........................ | 315/241 P |
| 5,428,495 A * | 6/1995 | Murphy et al. | ................. | 361/85 |
| 5,539,651 A * | 7/1996 | Zabar et al. | ..................... | 702/60 |
| 5,589,809 A | 12/1996 | Kogawa et al. | | |
| 5,715,129 A | 2/1998 | Innes | | |
| 5,864,458 A * | 1/1999 | Duffy et al. | .................. | 361/93.9 |
| 6,611,411 B2 * | 8/2003 | Williams et al. | ............. | 361/93.1 |
| 6,611,785 B1 * | 8/2003 | Yamanaka et al. | ........... | 702/155 |
| 6,731,193 B2 * | 5/2004 | Meier et al. | ................... | 336/200 |
| 6,813,123 B2 * | 11/2004 | Pihl | ................................ | 361/20 |
| 6,822,547 B2 * | 11/2004 | Saito et al. | ..................... | 336/200 |
| 6,856,515 B2 * | 2/2005 | Holce et al. | ................... | 361/752 |
| 6,950,292 B2 * | 9/2005 | Holce et al. | ..................... | 361/94 |
| 7,532,956 B1 * | 5/2009 | Pelaez et al. | ................. | 700/293 |
| 2005/0253544 A1 * | 11/2005 | Fitzgbbon et al. | ............ | 318/434 |
| 2005/0270707 A1 * | 12/2005 | Plemmons et al. | ............. | 361/23 |
| 2008/0208491 A1 * | 8/2008 | Burlak et al. | ................... | 702/58 |

* cited by examiner

*Primary Examiner* — Jared Fureman
*Assistant Examiner* — Scott Bauer
(74) *Attorney, Agent, or Firm* — Northwest IP Law Group, L.L.C.

(57) ABSTRACT

An electrical device protection apparatus, such as an overload relay, can include a microprocessor 102 that can receive a wide range of current signals from a current transformer or other current sensor. Also microprocessor 102 can employ a voltage sensor 112 to measure line voltage, for representing true power, and as a power supply 114 source for the microprocessor 102. The microprocessor can then generate annunciation signals 118, control signals 120, and/or communication signals 122 as necessary for the control and/or protection of an attached electrical device.

36 Claims, 4 Drawing Sheets

APPARATUS, SYSTEM, AND/OR METHOD FOR PROTECTION AND CONTROL OF AN ELECTRICAL DEVICE

RELATED APPLICATION

This application is a nonprovisional of, and claims the benefit of priority from, U.S. Provisional Patent Application No. 60/789,277, filed Apr. 4, 2006, which is hereby incorporated by reference in its entirety.

COPYRIGHT NOTICE

©2007 Cerus Industrial Corporation. A portion of the disclosure of this patent patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR §1.71 (d), (e).

TECHNICAL FIELD

The present application is in the field of industrial control systems, and more particularly, to protection and control mechanisms and/or methodologies for electrical motors and other electrical devices.

BACKGROUND

To protect an electric motor or other electrical device from damage due to an undesirable operating condition, such as an overload, under load, etc. industrial control systems can employ, as a standard power distribution method, a method of combining a relay, such as an overload relay, which is typically in the form of a thermal overload relay or an electronic overload relay, along with an electromagnetic contactor connected to a power circuit for the electric motor. In an overload operation, the electromagnetic contactor is allowed to cut off current to stop the electric motor.

Presently available thermal overload relays utilize heater and detector elements suitable for measuring only small amperage increments per each heater and detector element. Thermal overload relays typically have a small current adjustment range of 1.5:1, meaning the maximum setting is 1.5 times the lower setting. However, there are a wide variety of industrial control systems encompassing numerous current ranges that an overload relay may have to accommodate. This requires numerous sizes to be available in order to practically address common loads. For example, a typical IEC style contactor frame size is 45 mm wide and contactors switching up to 22 A are commonly manufactured in this single frame size. For this same 45 mm frame size, over 15 different thermal overload sizes are required (e.g., 0.1-0.16 A, 0.16-0.25 A, etc up to 16-22 A) to accommodate motor protective loads up to 22 A. The sheer number of thermal overload combinations is costly to inventory and can result in incorrectly ordered and/or incorrectly sized overloads being applied.

Compared to thermal overloads, electronic overloads are capable of measuring wider current ranges by utilizing current transformers. However, current transformers are subject to saturation, therefore accuracy degrades as the magnetics of the transformer staturate with increased current. This effectively limits the applicable current ranges. The current state of the art adjustment range of presently available electronic overload relays is typically limited to approximately 3.2 to 1, meaning the maximum setting is 3.2 times the lower setting. However, this still requires numerous overload sizes to be available to address the loads covered by a typical IEC 45 mm frame size contactor. In this frame size, up to 22 A is typically switched, yet over 5 different overload sizes can still be required (e.g., 0.1-0.32 A, 0.32-1.0 A, 1.0-2.9 A, 1.6-5.0 A, 3.7-12 A). Again, the sheer number of overload combinations is costly to inventory and can result in incorrectly ordered and/or incorrectly sized overloads being applied.

Electronic overloads require power for their circuitry, which poses certain challenges, as the readily available line voltage being switched is typically far in excess of the electronic overload power supply requirements (e.g. 480 VAC line voltage vs. 24 VAC electronic overload power required). With traditional electronic overloads, this necessitates the use of an external power supply. Certain models, such as Sprecher and Shuh CEP7, induce their power from the conductor being monitored using current transformers. However, this technique has limitations, as the current transformers are also used for measurement and subject to limited current measurement range.

U.S. Pat. No. 5,715,129 ("Innes"), issued Feb. 3, 1998, teaches an electronic overload relay having a power supply in series with the normally closed contact of the overload relay. The power supply is an integral element of the electronic overload relay in Innes. The relay is connectable to an electromagnetic contactor in keeping with conventions of thermal overload relays wherein the contactor coil is connected in series with the normally closed contact of the relay, and therefore also in series with the power supply to provide power for the overload relay when power is supplied to the contactor coil. A processor in the electronic overload relay is instructed to assume a sleep (low power consumption) mode during the closing of the contactor. A semiconductor switch in the power supply is operated by the processor in low voltage coil applications to directly connect the coil of the contactor in shunt of the power supply for the relay while the contactor closes. However, while providing a technique to power the electronic overload circuitry, the device in Innes is dependent on contactor coil voltage being in a suitable range for direct input to the electronics circuitry (e.g., 24VAC). In practice, contactors are often controlled through a push button or actuated using line voltages through the contactor coil. In these instances, utilizing coil voltages to power the contactor would not be feasible due to high line voltages (e.g. 480VAC) incompatible with the device.

U.S. Pat. No. 5,589,809 ("Kogawa et al."), issued Dec. 31, 1996, relates to an adjusting dial of a thermal overload relay for adjusting a working current of the thermal overload relay, and, more specifically, to a structure of the relay which can prevent an adjusting dial previously set from being mis-readjusted. However, Kogawa et al. still requires an initial manual setting of the thermal overload for the proper load rating, which is a labor intensive process and potentially subject to error.

Both thermal and electronic overloads require field calibration in order to establish the set-point of the normal full load amperage of the load monitored. Field calibration is a manual task, and as such, can be expensive and prone to human error. As a result, equipment may not be properly protected, nuisance trips may result, and life safety issues may arise should an overload be improperly sized or adjusted.

SUMMARY

The present application presents methods, apparatuses, and/or systems for providing automatic protection and/or control of electrical motors and/or other electrical devices. Embodiments as disclosed in the present application can substantially satisfy many of the needs unfulfilled by mechanisms previously available for the protection and control of electrical devices. One or more present embodiments can provide for wide-range current measurement, self-calibration, and wide-range line-powered electronics to provide application flexibility and/or reliable, cost-effective installation. In one embodiment, an overload relay can be employed along with an electromagnetic contactor, consistent with the present application, as a component in industrial control systems. For example, such an embodiment can be implemented as a component in a starter mechanism for electrical motors, pumps, or similar devices.

One embodiment can encompass an electrical measurement and/or control apparatus substantially suitable for motor protection and/or industrial control that can measure current ranges that are substantially wide in comparison to those measured by traditional thermal or electronic overload relays. The substantially broader applicability achieved by implementing such an embodiment can substantially reduce the number and/or type of overload relays (or other applicable electrical device protection mechanisms) required to be stored in inventory in order to accommodate the various amperage ranges that may be encountered in various control systems. This can allow for a substantial reduction in the amount of costly inventory that has to be maintained.

One or more embodiments consistent with the present application can implement auto-calibrating functionality that can prove advantageous in addressing overload, under load, and/or other undesirable operating conditions and/or parameters that may be encountered in industrial control systems, such as power distribution systems, as but one example. One embodiment can encompass an electrical measurement and control apparatus that can discern load types and levels and set motor set points or other appropriate control parameters substantially automatically. In addition, or in the alternative, an embodiment can encompass an electrical measurement and/or control apparatus that can discern load types and levels and set motor under load set points substantially automatically (e.g. to establish proof of flow conditions for fans and pumps, as but one example). Such embodiments can substantially reduce the need for manual field calibration, which can, at least in part, reduce labor requirements for installation and increase accuracy and reliability of installation.

In an alternative embodiment, an overload relay or other control device can be provided which can accommodate a range of current, voltage, and/or other parameter values, but also accept at least some amount of manual input to fine tune, filter, or otherwise aid in the identification and/or selection of overload set points and/or other operating ranges and/or parameters. Such an alternative embodiment can be offered based, at least in part, on design choice considerations, and/or it can be offered based, at least in part, on economic considerations, such as if a manual-input device can be manufactured more economically than devices solely enabling fully-automatic calibration. By allowing variable accommodation of a wide range of potential input values, such an embodiment can offer functionality in a variety of applications or system environments. The embodiment can substantially provide this functionality in a single device, rather than requiring a separate, statically set device to be purchased and inventoried for each potentially desirable value.

One embodiment consistent with the present application can encompass an electrical measurement and/or control apparatus that can be line powered over a wide range of currents and voltages, substantially reducing the need for external power supplies or dependence on costly current transformers. In addition, or in the alternative, an embodiment can encompass an electrical measurement and/or control apparatus that can be line powered to enable sensing of voltage, in addition to current in a conducting wire, to allow for substantially true power measurement and a resulting substantially superior load level detection.

For convenience, manufacturing efficiencies, cost savings, and/or other reasons, embodiments as disclosed herein can be provided as one or more electrical measurement and/or control apparatuses that can be constructed in a substantially unitary housing that can facilitate substantially simplified connection to a control device, such as a magnetic contactor, as but one example, to comprise a starter for electronic motors or other electronic devices.

Additional aspects and advantages of this invention will be apparent from the following detailed description of preferred embodiments, which proceeds with reference to the accompanying drawings.

DETAILED DESCRIPTION

Figure 1:
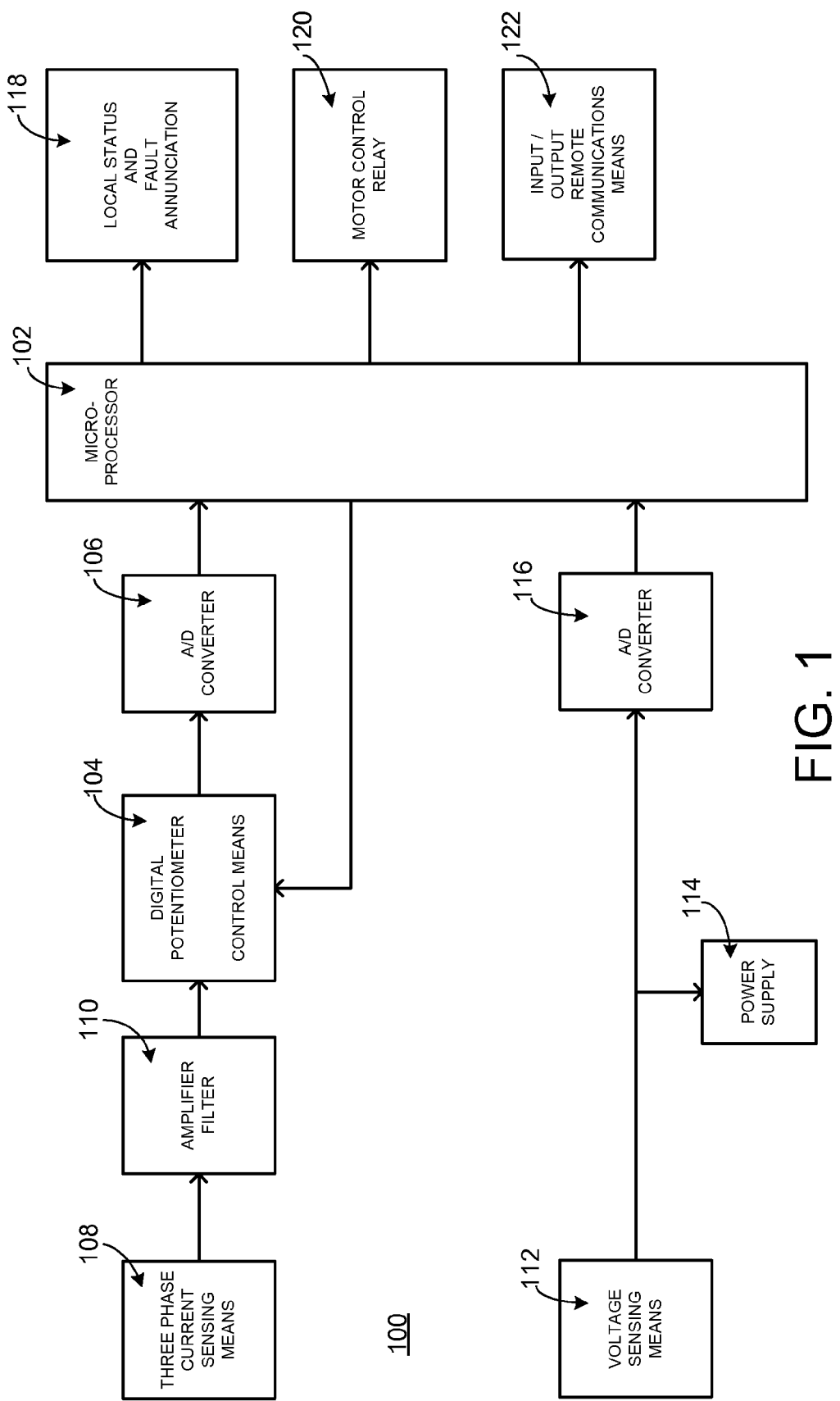
FIG. 1 illustrates one embodiment of an industrial control system for the automatic protection and/or control of electrical motors and/or other electrical devices.

As disclosed in the present application, one or more embodiments can be provided encompassing methods, apparatuses, and/or systems that can provide substantially automatic protection and/or control of electrical motors and/or other electrical devices in power distribution and/or other industrial control systems. FIG. 1 illustrates one embodiment of an industrial control system consistent with the present application. With reference to FIG. 1, the control system 100 includes a microprocessor 102 that receives signals from a current sensor 108 through an amplifier/filter 110 to a digital potentiometer 104 (or other prescaler and control mechanism), via an analog to digital converter 106. Also, microprocessor 102 can employ a voltage sensor 112 to measure line voltage to represent true power, and as a power supply 114 for the microprocessor 102. The microprocessor can then generate annunciation signals 118, control signals 120, and/or communication signals 122. Those skilled in the relevant arts will readily appreciate that additions, deletions, and/or modifications can be made to the system illustrated in FIG. 1, and/or the components illustrated therein, without departing from the scope of the present invention.

At least in part to help substantially accommodate the potentially wide variety of start-up and/or operating conditions an industrial control system can exhibit, one or more embodiments consistent with the present application can include, without limitation, circuitry and/or control logic for providing, at least in part, auto-calibration functionality over a wide range of circuit conditions and/or parameters. For example, an embodiment consistent with the present application can measure a wide range of current levels. For example, in one such embodiment, measured current levels can range from 0.1-40 Amperes. With such an embodiment, a single device consistent with principles disclosed in this application can accommodate the up to 22 A commonly manufactured in typical IEC-style contactors with a frame size of 45 mm wide. Of course, these current ranges are provided for illustrative purposes only, and not by way of limitation on the claimed subject matter. Embodiments with such auto- or self-calibrating features can, for example, automatically detect and substantially accommodate a wide variety of operating characteristics exhibited by the potentially numerous types and/or classes of motors and/or other electrical devices than can be supplied by equipment manufacturers.

As one example of a device implemented at least in part to provide auto-calibration functionality, one embodiment can employ a microprocessor suitable for sampling current and/or voltage characteristics. One or more microprocessor embodiments can be provided to take samples at a high frequency. For example, one embodiment of a microprocessor can enable sampling at a rate of 4 MHz. If that microprocessor employs a 5 MHz analog to digital converter, as but one example, it can substantially conduct measurements at a rate of four per millisecond. One or more microprocessor embodiments consistent with the present application can employ an algorithm and/or control logic to automatically determine and set the correct set point for overload applications for a motor or other electrical device (as but one example) based, at least in part, on such factors as current in-rush, phase-angle, and/or other load characteristics that are typically representative of a particular class of electrical device. As but one example, provided for illustrative purposes only and not by way of limitation, detecting the amplitude of the starting wave and phase angle of the initial starting voltage can allow the microprocessor to identify the type or class of electrical device coupled to the power distribution line. Another embodiment can measure the ratio of in-rush current to full load current as and an indicator of electrical device class. For example, a ratio of 6:1 can indicate a Class B electrical motor, whereas a ratio of 10:1 can indicate a Class F electrical motor, as but two examples.

In an alternative embodiment, the microprocessor can generate an interrogation signal to ping the electrical device for identification purposes. A return signal received by the microprocessor, or a circuit characteristic identified by the microprocessor in response to the interrogation signal, can be used to identify and classify the associated electrical device.

After determining class (which characterizes the type and/or size of motor or other connected electrical device), through use of an interrogation signal, or from measurements of the initial voltage and other startup information, the microprocessor can generate (or allow one or more other controllers to generate) signals to control the system at or below a particular desired running voltage range, given the device class/type detected. Over/under voltage and/or frequency can be similarly determined. In addition, or in the alternative, the microprocessor can employ one or more algorithms and/or control logic to discern loss of load to a motor based on rapid changes in amperage or power. This helps protect an attached electrical device, such as, for example, with where there is a broken fan belt, dry pumping situation, and/or other undesirable condition affecting an electrical device. A microprocessor embodiment can operate a motor or other electrical device at a desired service level by dialing down trip points, as but one example.

Figure 2:
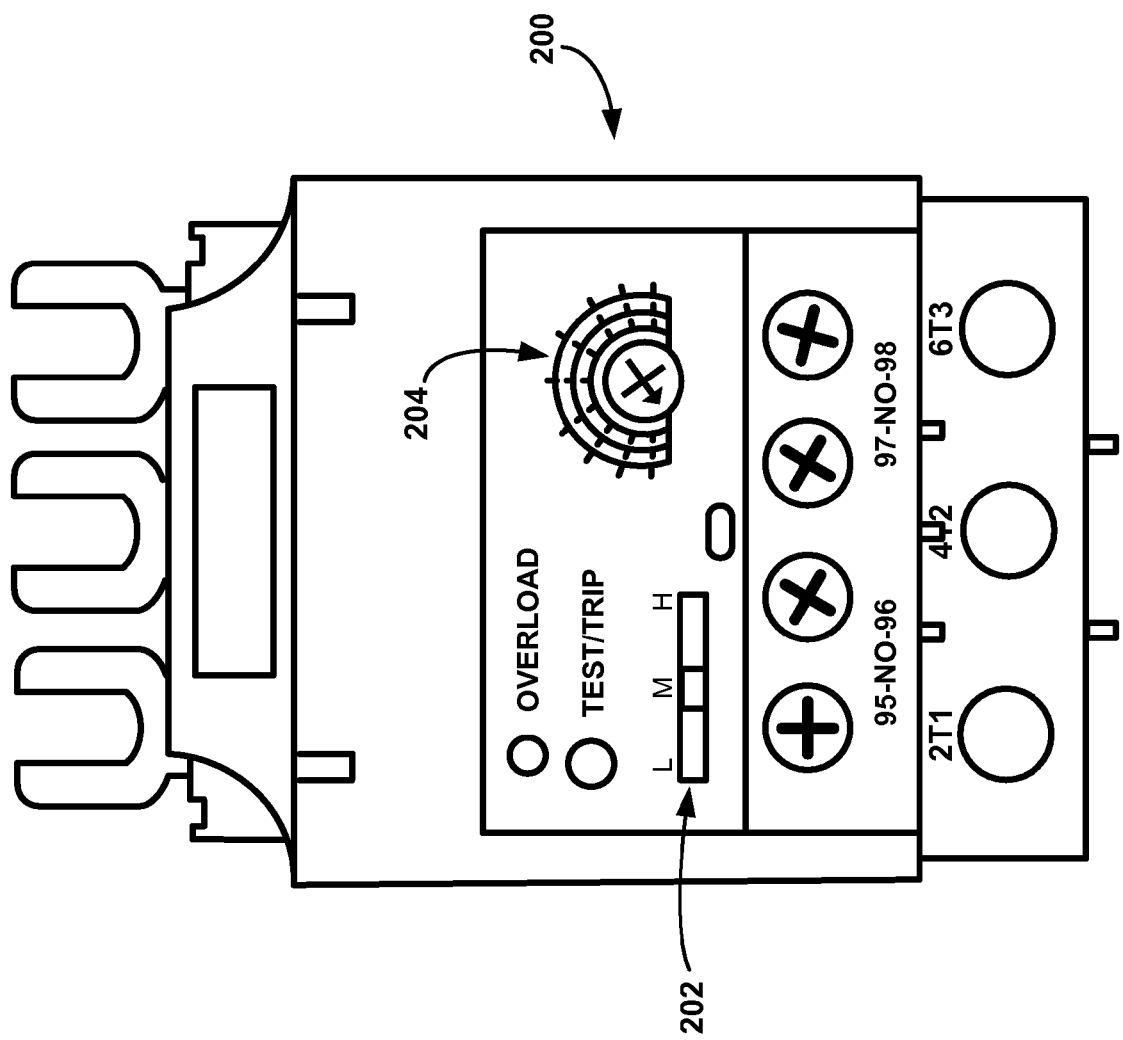
FIG. 2 illustrates one embodiment of an at least partially manually switched variable relay.

In an alternate embodiment, an overload relay or other control device can be provided which can accommodate a range of current, voltage, and/or other parameter values, but also accept at least some amount of manual input to aid in the identification and/or selection of overload set points and/or other operating ranges and/or parameters. FIG. 2 illustrates one example of an overload device embodiment 200 that can accept manual input. As illustrated in FIG. 2, a selector switch 202 can be provided for a user to manually select from among one or more predetermined values and/or ranges that can represent subsets within the entire range of values embodiment 200 can accommodate. For example, selector switch 202 can be set to "L" to accommodate a relatively low input value, "M" to accommodate a relatively mid-range value, or "H" to accommodate a relatively high input value. If, for example, embodiment 200 can accommodate input electrical current values ranging from 0.1 A-40 A, the settings for L, M, and H can be defined to represent 0.1 A-1.6 A, 1.6 A-8 A, and 8 A-40 A, respectively. To implement a particular selected value, selector switch 202 can change a burden resistor for a current transformer. Of course, such values and ranges are presented for illustrative purposes only. These example values are not intended to limit the scope of the subject matter presented in the current application. An alternative embodiment can employ a different quantity of settings. For example it could have L, M1, M2, and H settings, as but one other example. This and other such variations are equally within the scope of the claimed subject matter.

As an example of an additional and/or alternate control mechanism, a control dial 204 can be provided to select and/or fine tune operating values. For example, control dial 204 illustrates three graduated indices of selectable values arranged in substantially concentric circles around the dial, with each index corresponding to one of the predetermined value ranges selectable using selector switch 202. Of course, those skilled in the relevant art will appreciate that alternate types, quantities, configurations, and/or arrangements of manual inputs could also be employed.

To help accommodate the wide range of initial or operating conditions power distribution or other industrial control systems can exhibit, one or more embodiments as disclosed in the present application can, at least in part, employ circuit design and/or electronic circuit elements intended substantially to tolerate a broad range of potential voltage measurements and/or other inputs. As one example, a Rogowski current transformer can be employed in accordance with one such embodiment. One embodiment of a Rogowski current transformer can consist of a torriod provisioned over a cylindrically shaped core and fabricated of non-magnetic material for measuring current with increased accuracy over wide ranges with increased immunity to core saturation. This presents advantages over ferrite core current transformers. Such an embodiment can provide substantially superior motor protection in comparison to traditional ferrite core current transformers or thermal overload elements. In addition, or in the alternative, a differential noise canceling loop can be employed to improve the accuracy of measurement at low current input levels with increased immunity to electromagnetic interference. For example, if currents below 1 Ampere are experienced, use of a noise canceling loop in addition to the Rogowski current transformer can yield advantageous results.

In one embodiment, Rogowski current transformers can be fabricated directly onto a printed circuit board for cost effective manufacturing and accurate reproduction. Such an embodiment can be provided as a stand-alone element, or integrated with one or more other control elements to form an electrical starter or other control device, as but one example. One Rogowski current transformer embodiment can be torriodally wound in a substantially oblong shape to enhance signal gain for low current applications. Based, at least in part, on the ability of one or more embodiments implementing a Rogowski current transformer to accommodate a wide input voltage range, such embodiments can sample input voltage directly from a line power supply. Sampling directly from the line power supply can substantially simultaneously power the device and provide voltage input signals that enable a substantially true power measurement. A circuit can employ a voltage resister/divider to scale down the line voltage to a range that facilitates operation of the microprocessor (e.g., 5V, as but one example). Sensing substantially true power facilitates embodiments in determining various forms of useful information in a given industrial application (such as determining if a belt on a motor is broken, as but one example)

One or more present embodiments can employ an analog to digital converter ("ADC") to convert initial analog voltage data into digital form for use by a microprocessor. Because of the potentially large variability in voltage or current, or other initial conditions, that an embodiment can experience at startup, embodiments can employ ADCs and microprocessors that can be pre-selected with resolution characteristics substantially sufficient to accommodate the line characteristics the embodiment is expected to encounter. For example, by employing a microprocessor with sufficient resolution, one embodiment can encompass a single product with the ability to detect and accommodate wide ranging input currents, e.g, ranging from 0.1 to 40 Ampere, as but one example. Of course, such a range is presented as but one example for illustrative purposes and not by way of limitation on the present subject matter. By way of further illustration, one embodiment can employ an 18-bit ADC. However, for manufacturing ease, cost considerations, design optimization, and/or other reasons, alternate resolution devices could be used. For example an alternative embodiment can be provided to substantially accommodate a variable range by employing a 10-bit device with a prescaler device such as a digital potentiometer, pulse-width modulator, amplifier, analog prescaler, voltage controlled amplifier, gain controller circuits, and/or other companding or prescaling components provisioned in front of the ADC to pre-scale the input signal to a range the 10-bit device can substantially accommodate. The prescaling components can be microprocessor controlled. With such embodiments, as well as other embodiments consistent with the present subject matter, auto-calibration functionality can be applied to the input signal.

Figure 3:
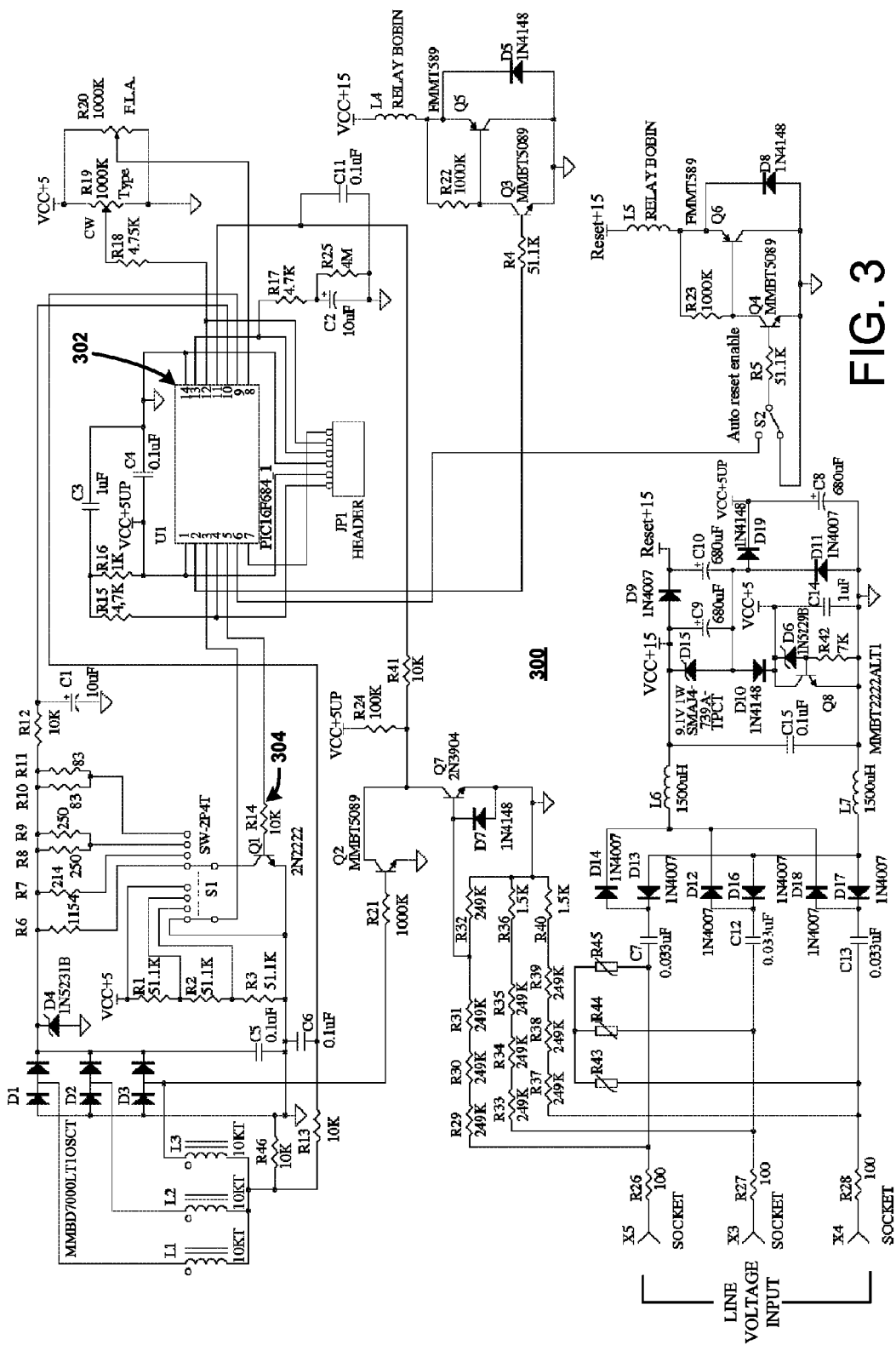
FIG. 3 illustrates one example of a circuit diagram corresponding to an electrical device control apparatus embodied as an overload relay apparatus.

FIG. 3 illustrates one example of a circuit diagram corresponding to an electrical device control apparatus embodied as an overload relay apparatus. In particular, FIG. 3 illustrates a control circuit 300 including a microprocessor 302, a pulse-width modulator 304 representing a prescaler for scaling a measured signal for input to an ADC. Also with particular reference to the circuit elements represented in FIG. 3, the current transformer output is rectified by elements D1, D2, and D3, applied to the pulse width modulator Q1 (304), and filtered by R12, C1 and input to ADC pin 10 of microprocessor U1 (302). It can also be noted, with reference to FIG. 3, that line voltage connections are reduced by a capacitor divider (C7, C12, C13) that feeds rectifiers (D14, D13, D12, D16, D17, and D18) and a voltage regulator (D15, D10, D6, and Q8) for supplying desired circuit operating voltage. Also, alarm output relays are energized from pins (2,6) of the microprocessor, 302, and driving transistors (Q5, Q6). Of course, the circuit diagram illustrated in FIG. 3 is presented as but one embodiment for illustrative purposes and to facilitate discussion. The claimed subject matter however is not limited in this regard.

Figure 4:
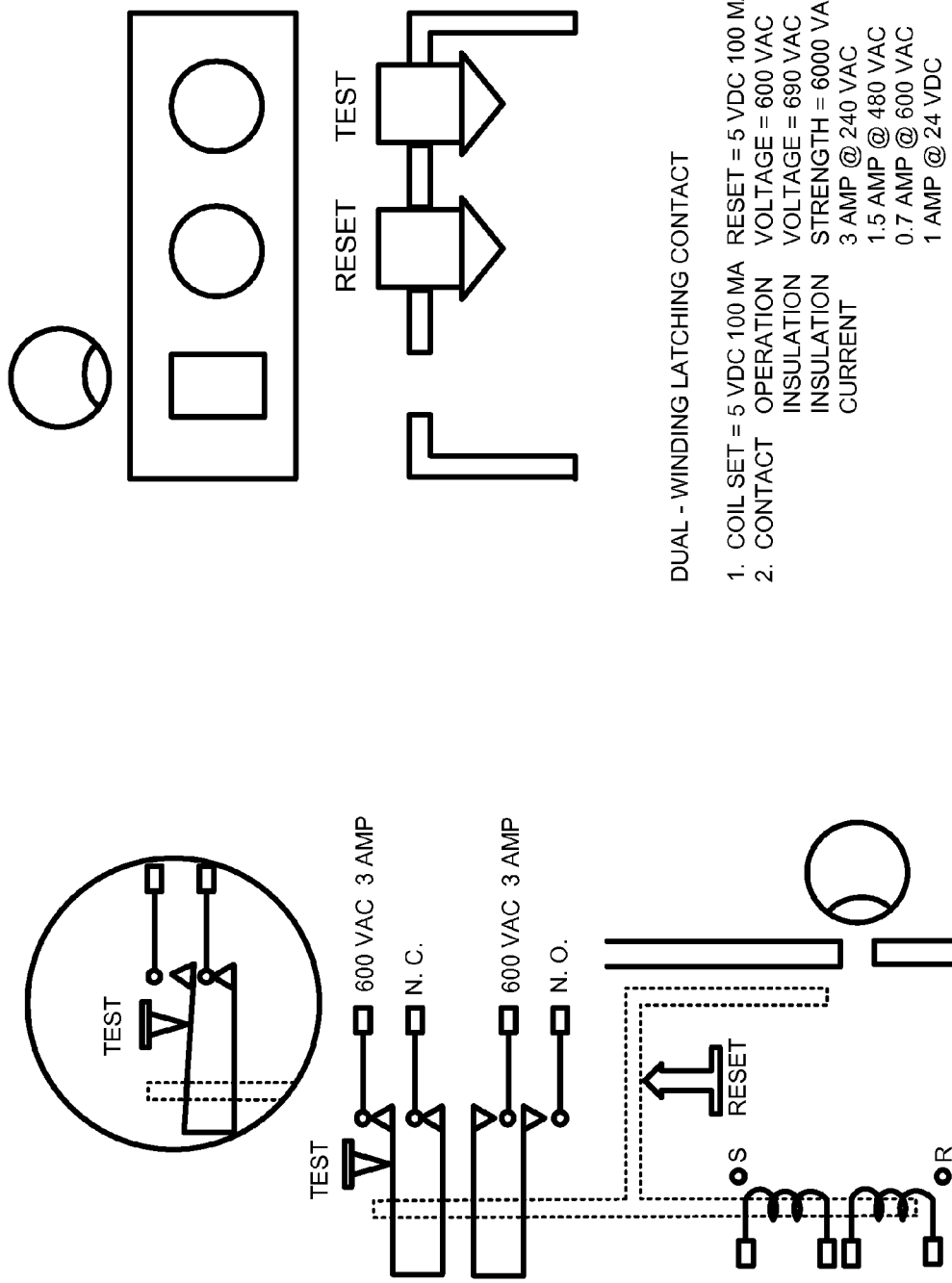
FIG. 4 presents a schematic of a latching contact relay according to one embodiment.

In one embodiment, automatic protection and/or control of electrical motors and/or other electrical devices can be facilitated by employing a latching contact relay. FIG. 4 illustrates one example of a latching contact relay embodiment. A pulse of sufficient magnitude can energize the relay, and thereafter the relay can remain in its energized state until current in the coil is reversed, or the relay is manually and/or otherwise reset. An embodiment employing a latching contact relay can function with reduced energy demands, thus helping reduce overall system costs. Additionally, a latching contact relay can be set directly on a printed circuit board and provided as a component of a control device, or it can be provided as an integrated part of the housing for an industrial control starter mechanism or other control mechanism, as but two illustrative embodiments.

One or more embodiments as disclosed above can comprise and/or be provided as a stand alone protection device embodiment (for example, by being set on a printed circuit board). Such a stand alone embodiment can allow for substantially convenient and/or custom integration into existing and/or legacy industrial control systems. In the alternative, an embodiment can be provided in a single unitary housing which can align and support voltage input pins in conjunction with current transformer apertures for substantially simplified connection to one or more control devices, such as a mechanical contactor, to comprise a starter, as but one example presented for illustration and not by way of limitation.

It will be obvious to those having skill in the art that many changes may be made to the details of the above-described embodiments without departing from the underlying principles of the invention. The scope of the present invention should, therefore, be determined only with respect to the claimed subject matter.

The invention claimed is:

1. An apparatus for providing overload thermal protection and control of a motor or electrical device having a motor, comprising:
   a current transformer provisioned for measuring power supply line current supplied to a motor or electrical device having a motor, with substantial accuracy over a wide current range; and
   a microprocessor configured for:
   receiving a current input signal corresponding to the power supply line current measured by the current transformer;
   receiving a voltage input signal corresponding to a voltage measured from the power supply line powering the motor or electrical device having a motor;
   identifying a classification of the motor or electrical device having a motor, and a corresponding overload thermal protection value, based, at least in part, on at least one of the received current input signal or the received voltage input signal; and
   implementing control logic to set a set point for operating the motor or electrical device having a motor consistent with the identified classification and corresponding overload thermal protection value.

2. The apparatus of claim 1, wherein the microprocessor derives operating power from the power supply powering the motor or electrical device having a motor.

3. The apparatus of claim 1, wherein the microprocessor identifies the classification of the motor or electrical device having a motor by comparing an in-rush current to a full load current for the motor or electrical device having a motor.

4. The apparatus of claim 1, wherein the microprocessor identifies the classification of the motor or electrical device having a motor based, at least in part, on a phase-angle load characteristic.

5. The apparatus of claim 1, wherein the microprocessor is programmed to discern loss of load to the motor or electrical device having a motor in response to detecting rapid changes in amperage or power.

6. The apparatus of claim 1, wherein the microprocessor is configured to send an interrogation signal to the motor or electrical device having a motor and, in response to sending the interrogation signal, receive a return signal or identify a circuit characteristic for use in identifying the classification of the motor or electrical device having a motor.

7. The apparatus of claim 1, wherein the current transformer is constructed of a material substantially resistant to core saturation.

8. The apparatus of claim 7, wherein the material is non-magnetic.

9. The apparatus of claim 1, wherein the current transformer is a Rogowski current transformer.

10. The apparatus of claim 9, wherein the Rogowski current transformer is printed on a printed circuit board.

11. The apparatus of claim 10, wherein the microprocessor is mounted to the printed circuit board.

12. The apparatus of claim 9, wherein the Rogowski current transformer is torroidally wound over a cylindrically shaped core so as to to enhance signal gain for low current applications.

13. The apparatus of claim 9, further comprising a differential noise canceling loop circuit to substantially resist electromagnetic interference and enable accurate current measurement at a low current input value.

14. The apparatus of claim 13, wherein the low current input values correspond to a current below 1 Ampere.

15. The apparatus of claim 1, wherein the wide current range corresponds to a range substantially between 0.1-40 Amperes.

16. The apparatus of claim 1, further comprising an analog to digital converter.

17. The apparatus of claim 16 wherein the analog to digital converter is an 18-bit converter.

18. The apparatus of claim 16, wherein the analog to digital converter is a 10-bit converter.

19. The apparatus of claim 18, further comprising a pre-scaler circuit element to scale a signal input to the analog to digital converter.

20. The apparatus of claim 19, wherein the pre-scaler is a digital potentiometer or pulse width modulator.

21. The apparatus of claim 1, further comprising at least one manual control to limit the current transformer to measuring within an expected subset current range, the expected subset current range being a limited range within the wide current range.

22. The apparatus of claim 1, further comprising a latching contact relay.

23. The apparatus of claim 1, further comprising voltage input pins provisioned in conjunction with current transformer apertures for connection to a secondary control device.

24. The apparatus of claim 23, wherein the secondary control device is a mechanical contactor.

25. A method, comprising the steps of:
using a current transformer electromagnetically coupled to a power supply line, measuring at least one of an input signal or circuit characteristic of a power distribution circuit electromagnetically connected to a motor or electrical device having a motor;
based at least in part on the measured input signal or circuit characteristic, classifying the motor or electrical device having a motor; and
setting an overload thermal protection set point for the motor or electrical device having a motor based at least in part on the classification of the motor or electrical device having a motor.

26. The method of claim 25, wherein the measuring step includes measuring a load characteristic of the motor or electrical device having a motor.

27. The method of claim 26, wherein the load characteristic includes in-rush current.

28. The method of claim 26, wherein the load characteristic includes a phase-angle.

29. The method of claim 25, wherein
the measuring step includes sending an interrogation signal and either receiving a response signal or detecting a circuit characteristic; and
the classifying step is based, at least in part, on the received response signal or detected circuit characteristic.

30. The method of 25, further comprising the step of drawing operating power from a line power source supplying power to the power distribution circuit, the operating power being used for conducting the measuring, classifying, and setting steps.

31. A system for controlling and providing thermal protection for a motor or electrical device having a motor, comprising:
a power supply line providing power to an a motor or electrical device having a motor;
a contactor relay for disconnecting power supplied to the motor or electrical device having a motor, via the power supply line, in response to an undesirable operating condition being determined to exist in the motor or electrical device having a motor; and
an overload protection relay including:
a current transformer for measuring current supplied to the motor or electrical device having a motor via the power supply line;
a microprocessor for identifying the motor or electrical device having a motor and setting one or more corresponding overload thermal protection set points to detect an occurrence of the undesirable operating condition in the motor or electrical device having a motor.

32. The system of claim 31, wherein the undesirable operating condition is an overload on the motor or electrical device having a motor.

33. The system of claim 31, wherein the undesirable operating condition is an under load on the motor or electrical device having a motor.

34. The system of claim 31, wherein the undesirable operating condition is an overload or an under load on the motor or electrical device having a motor.

35. The system of claim 31, wherein the contactor relay and the overload protection relay are provisioned in a single housing.

36. The system of claim 35, wherein the single housing corresponds to a starter mechanism for the motor or electrical device having a motor.

* * * * *